United States Patent
Esfahani et al.

(10) Patent No.: US 10,022,311 B1
(45) Date of Patent: Jul. 17, 2018

(54) KERATIN DELIVERY PROCESS BY REACTIVE CHEMICAL COMPOSITION FOR IMPROVED METHODS OF STRENGTHENING AND SMOOTHING HAIR

(71) Applicants: Jozef Magran Esfahani, Valley Village, CA (US); Amy Luu, Valley Village, CA (US); Cheri Kluft, Montecito, CA (US)

(72) Inventors: Jozef Magran Esfahani, Valley Village, CA (US); Amy Luu, Valley Village, CA (US); Cheri Kluft, Montecito, CA (US)

(73) Assignee: JACK BRANDS, LLC, Montecito, CA (US)

( * ) Notice: Subject to any disclaimer, the term of this patent is extended or adjusted under 35 U.S.C. 154(b) by 0 days.

(21) Appl. No.: 15/149,343

(22) Filed: May 9, 2016

Related U.S. Application Data

(60) Provisional application No. 62/159,272, filed on May 9, 2015.

(51) Int. Cl.
*A61K 8/36* (2006.01)
*A61K 8/365* (2006.01)
*A61Q 5/04* (2006.01)
*A61K 8/34* (2006.01)

(52) U.S. Cl.
CPC .............. *A61K 8/36* (2013.01); *A61K 8/345* (2013.01); *A61K 8/365* (2013.01); *A61Q 5/04* (2013.01)

(58) Field of Classification Search
None
See application file for complete search history.

(56) References Cited

U.S. PATENT DOCUMENTS

2013/0306095 A1* 11/2013 Syed .............. A61K 8/447
132/204

OTHER PUBLICATIONS

European Commission, Methylene Glycol in Hair Straighteners, Jun. 2012 (Year: 2012).*
Scientific Committee on Consumer Safety , Opinion on Methylene glycol , Jun. 26-27, 2012 (Year: 2012).*

* cited by examiner

*Primary Examiner* — Jennifer A Berrios
(74) *Attorney, Agent, or Firm* — Cislo & Thomas, LLP

(57) ABSTRACT

The disclosure comprises a process that pertains to the chemical reaction of hair when exposed to a series of chemical compositions. Utilization of named ingredients in specified order manipulates the pH value and driving agents; the nature of the process is an improvement of delivery methods for hair strengthening and smoothing treatments.

15 Claims, 3 Drawing Sheets

KERATIN DELIVERY PROCESS BY REACTIVE CHEMICAL COMPOSITION FOR IMPROVED METHODS OF STRENGTHENING AND SMOOTHING HAIR

CROSS-REFERENCE TO RELATED APPLICATION

This patent application claims the benefit of U.S. Provisional Patent Application Ser. No. 62/159,272, filed May 9, 2015, which application is incorporated in its entirety here by this reference.

DESCRIPTION OF INVENTION

Figure 1:
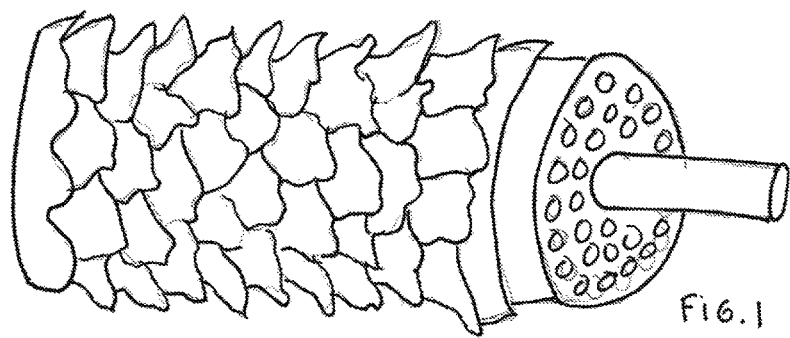
FIG. 1 as a whole shows the structure of the hair: Outer Cuticle Layer, Internal Cortex, Center Medulla. When the hair is exposed to "Formula 1", the cuticle scales rise.
Figure 2:
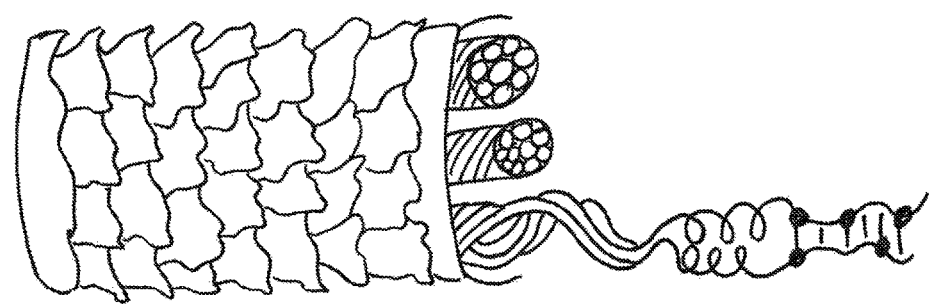
FIG. 2 shows the alpha helix within the cortex. Within the alpha helix, this illustration signifies the missing keratin protein molecules and unlocked disulfide bonds.
Figure 3:
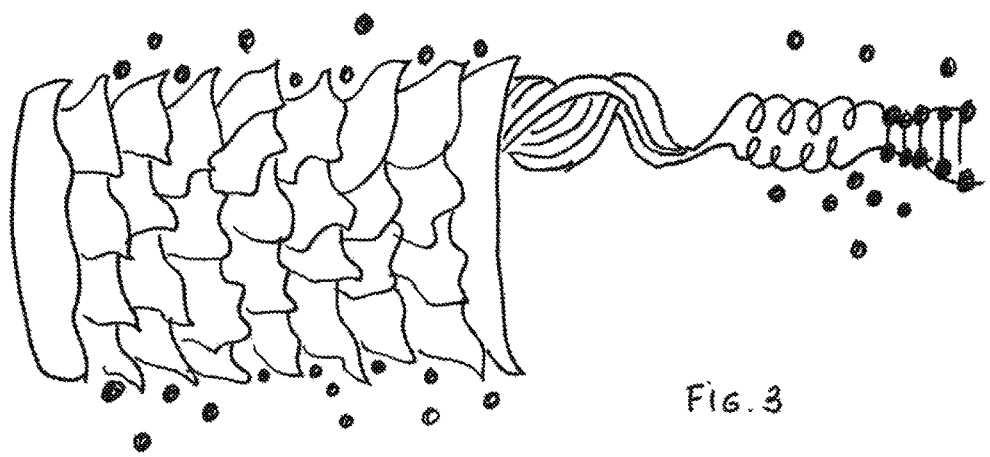
FIG. 3 is an illustration of the Cashmilan LS 9604 keratin protein molecules entering the cuticle layer and attaching to disulfide bonds that do have a paired protein structure.
Figure 4:
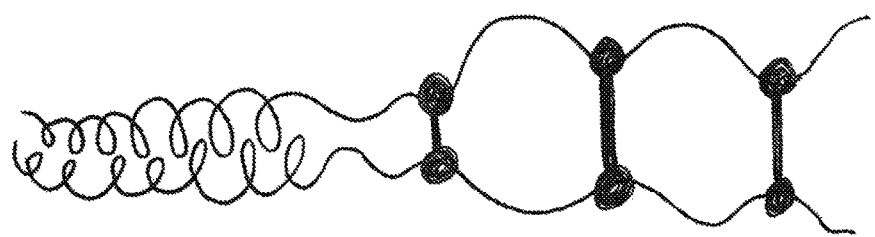
FIG. 4 shows the Cashmilan Ls 9604 keratin protein molecule has made a corresponding connection to the disulfide bond.
Figure 5:
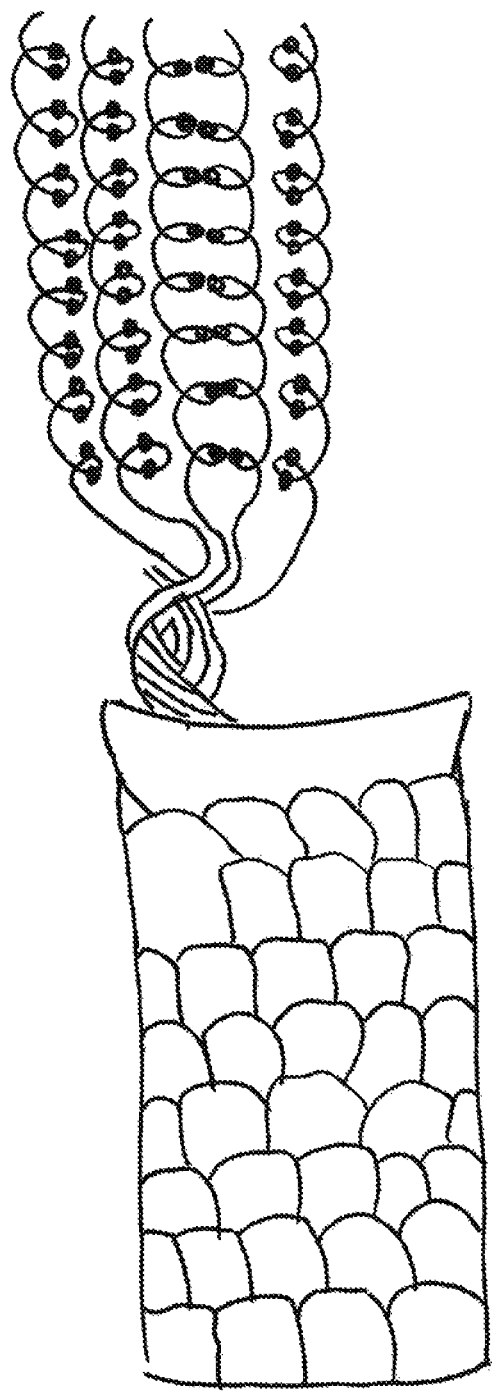
FIG. 5 is an illustration after the hair has been dried and flat ironed with "Formula 2". The outer cuticle layer of the hair is smooth and uniform. Internally, the alpha helix has uniform Cashmilan Ls 9604 keratin protein molecules and disulfide bond connections.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

This invention pertains to the application process and methods of hair strengthening and smoothing treatments as the hair is taken through multiple processes of chemical reactions. When hair is exposed to chemical processes (i.e demi-permanent hair color, permanent hair color and lighteners), thermal styling and exposed to free radicals, the hair is susceptible to damage internally and externally. Damage refers to the loss of keratin protein and the missing scales of the cuticle layer. This method is intended to replenish missing keratin protein molecules to the internal structure of the hair and create a temporary strengthener to the external cuticle layer that has been lost or damaged during chemical process, thermal styling tools, and exposure to free radicals. This process embraces the ability to manipulate the cuticle barrier of the hair, unlock internal bonds within the cortex, and adequately replace hair identical proteins within the alpha helix to rebuild and reinforce the structure within the cortex.

The invention involves two main liquid compositions: "Formula 1" and "Formula 2". The active ingredient in "Formula 1" utilizes carboxylic acid and related acids. Closely related acids include Glycolic acids and Glyoxylic Acid. The active ingredient in "Formula 2" utilizes methanediol and related chemical compositions to allow the newly adhered keratin protein to cure and mend internally.

During application of "Formula 1", the hair initially reacts to the pH value of the formula. While the pH value of "Formula 1" is less than 6 at an acidic level, the hair is manipulated to raise the cuticle scales thus allowing access to the internal structure or the cortex of the hair. Based on the concentration percentage of the active ingredients, the hair is processed from 0-90 minutes to allowing the formula to control the amount the cuticle scales raise. As "Formula 1" is processing, the disulfide bonds (also known as sulfur-sulfur bonds) present in the hair cortex begin to gently unlock or release from one another to allow the alpha helix to obtain and conjoin with Cashmilan LS 9604, a hair identical protein molecule. Unlike treatments that utilize active ingredients such as sodium hydroxide, this chemical does not permanently disconnect or break bonds permanently thus changing the internal structure for the life of the hair.

Once the hair has been processed with "Formula 1" for the desired duration of time, "Formula 1" is rinsed thoroughly from the hair. Because the cuticle scales are now raised and the disulfide bonds have now disconnected, the hair is now adequately prepared to accept keratin protein in "Formula 2". Once the cuticle scales are raised, the keratin protein within "Formula 2" now have the ability to penetrate into the cortex and adhere to the areas where the alpha helix is missing keratin protein molecules.

After the hair has been rinsed from "Formula 1" the hair is to be saturated with "Formula 2" on towel dried hair to encourage even porosity. If the hair is of even porosity, the hair will be able to attract inserted Cashmilan LS 9604 only in the areas in which are necessary in the respects to the reparative aspect of the treatment without the over load of protein in unnecessary areas. Once "Formula 2" has been applied, the Cashmilan LS 9604 locates the areas in which the alpha helix is lacking keratin protein. Following the saturation of "Formula 2", the hair is then blown dried with the solution in the hair. Drying "Formula 2" into the hair allows for the newly penetrated Cashmilan LS 9604 (hair identical keratin protein molecules derived from sheep's wool) to hold its connection to the disulfide bonds and allowing keratin protein to curing into the structure of the alpha helix. Once the connection has been made and the hair is dried, a thermal straightening iron is then used to ensure the cuticle scales can then be reverted to its natural state. Given that there may be areas in which the cuticle layer of the hair has been degraded or missing, active methanediol or related chemical compositions create temporary protection barrier to prevent newly inserted keratin protein from releasing quickly or rinsing. When cuticle layer has finally been sealed and patched, the overall look and feel of the hair shows to be smoother and softer for the duration of time after the chemical process has been completed.

During the process of chemical reactions presented, the hair has now utilized the process to adequately address lost keratin protein molecules within the hair structure as a semi-permanent hair strengthening treatment internally and address the lack of universal cuticle scales to the external structure providing smoothing effects. Current inventions of treatments pertaining to hair strengthening or smoothing do not allow keratin protein molecules to enter into the structure of the hair strand but strengthen only the external layer of the hair strand.

What is claimed is:

1. A method of treating hair, comprising:
   a. treating the hair with a first formula comprising a carboxylic acid selected from the group consisting of glycolic acid and glyoxylic acid and hair identical protein molecules, wherein the first formula has a pH of less than 6, wherein treating the hair with the first formula raises cuticle scales of the hair to expose hair cortices, wherein the hair cortices comprise proteins configured in an alpha helix arrangement held together by disulfide bonds, wherein the first formula disconnects the disulfide bonds; and
   b. treating the hair with a second formula comprising methanediol causing the hair identical protein molecules to bind to the alpha helix; and
   c. reverting the hair cuticles back to their natural state using a thermal straightening iron.

2. The method of claim 1, wherein the carboxylic acid comprises glycolic acid.

3. The method of claim 1, wherein the hair is treated with the first formula for up to 90 minutes.

4. The method of claim 1, wherein the hair is blow dried with the second formula in the hair.

5. A method of treating hair, the hair comprising protein in an alpha helix configuration, the protein comprising keratin protein, the method comprising:
   a. raising cuticle scales of the hair out of a natural state to expose hair cortices, and disconnecting disulfide bonds within the hair cortices, using a first formula, the first formula comprising a carboxylic acid selected from the group consisting of glycolic acid and glyoxylic acid;
   b. exposing the hair cortices to hair identical protein molecules;
   c. causing the hair identical protein molecules to bind to the alpha helix by applying a second formula comprising methanediol; and
   d. reverting the cuticle scales back to the natural state using a thermal straightening iron.

6. The method of claim 5, wherein the carboxylic acid comprises glycolic acid.

7. The method of claim 5, wherein the first formula has a pH of less than 6.

8. The method of claim 5, wherein the carboxylic acid comprises glyoxylic acid.

9. The method of claim 5, wherein the hair is treated with the first formula for up to 90 minutes.

10. The method of claim 5, wherein the hair is blow dried with the second formula in the hair.

11. The method of claim 5, wherein the first formulation comprises glycolic acid in an aqueous solution up to 15 percent.

12. The method of claim 5, wherein the methanediol is present in amounts up to 8% by weight of the second formulation.

13. The method of claim 5, wherein the hair identical protein molecules comprise keratin protein molecules obtained from Cashmere Sheep's Wool.

14. The method of claim 5, wherein the hair identical protein molecules are keratin protein molecules comprising vegetable based protein.

15. The method of claim 1, wherein the carboxylic acid comprises glyoxylic acid.

* * * * *